(12) United States Patent
Filippov et al.

(10) Patent No.: US 8,691,537 B2
(45) Date of Patent: Apr. 8, 2014

(54) **METHOD FOR PRODUCING AN L-AMINO ACID USING A BACTERIUM OF THE *ENTEROBACTERIACEAE* FAMILY WITH ATTENUATED EXPRESSION OF THE RCSA GENE**

(75) Inventors: Dmitriy Vladimirovich Filippov, Moscow (RU); Elvira Borisovna Voroshilova, Moscow (RU); Mikhail Markovich Gusyatiner, Moscow (RU)

(73) Assignee: Ajinomoto Co., Ltd., Tokyo (JP)

( * ) Notice: Subject to any disclaimer, the term of this patent is extended or adjusted under 35 U.S.C. 154(b) by 898 days.

(21) Appl. No.: 12/323,893

(22) Filed: Nov. 26, 2008

(65) Prior Publication Data
US 2009/0137011 A1 May 28, 2009

Related U.S. Application Data

(63) Continuation of application No. PCT/JP2007/061237, filed on May 28, 2007.

(60) Provisional application No. 60/868,102, filed on Dec. 1, 2006.

(30) Foreign Application Priority Data

Jun. 1, 2006 (RU) .............................. 2006118967

(51) Int. Cl.
| | | |
|---|---|---|
| C12P 13/24 | (2006.01) |
| C12P 13/04 | (2006.01) |
| C12P 13/22 | (2006.01) |
| C12P 13/20 | (2006.01) |
| C12P 13/14 | (2006.01) |
| C12P 13/12 | (2006.01) |
| C12P 13/08 | (2006.01) |
| C12P 13/06 | (2006.01) |
| C12N 1/20 | (2006.01) |
| C07K 14/00 | (2006.01) |
| C07H 21/04 | (2006.01) |

(52) U.S. Cl.
USPC ........... 435/107; 435/106; 435/108; 435/109; 435/110; 435/113; 435/115; 435/116; 435/252.3; 435/252.33; 530/350; 536/23.7

(58) Field of Classification Search
None
See application file for complete search history.

(56) References Cited

U.S. PATENT DOCUMENTS

| 5,175,107 A | 12/1992 | Debabov et al. |
| 5,688,671 A | 11/1997 | Sugimoto et al. |
| 5,932,453 A | 8/1999 | Kikuchi et al. |
| 6,132,999 A | 10/2000 | Debabov et al. |
| 6,303,348 B1 | 10/2001 | Livshits et al. |
| 6,319,696 B1 | 11/2001 | Kishino et al. |
| 7,138,266 B2 | 11/2006 | Debabov et al. |
| 7,186,531 B2 | 3/2007 | Akhverdian et al. |
| 7,259,003 B2 | 8/2007 | Livshits et al. |
| 7,312,058 B2 | 12/2007 | Kashiwagi et al. |
| 7,381,548 B2 | 6/2008 | Sheremet'eva et al. |
| 7,422,880 B2 | 9/2008 | Rybak et al. |
| 2002/0110876 A1 | 8/2002 | Miyata et al. |
| 2003/0092026 A1 | 5/2003 | Rey et al. |
| 2004/0132165 A1 | 7/2004 | Akhverdian et al. |
| 2004/0229311 A1 | 11/2004 | Hirano et al. |
| 2004/0229320 A1 | 11/2004 | Stoynova et al. |
| 2005/0214911 A1 | 9/2005 | Marchenko et al. |
| 2005/0239175 A1 | 10/2005 | Tabolina et al. |
| 2005/0239177 A1 | 10/2005 | Livshits et al. |
| 2006/0088919 A1 | 4/2006 | Rybak et al. |
| 2006/0216796 A1 | 9/2006 | Hashiguchi et al. |
| 2007/0004014 A1 | 1/2007 | Tsuji et al. |
| 2008/0009041 A1* | 1/2008 | Mizoguchi et al. .......... 435/71.1 |
| 2008/0113416 A1 | 5/2008 | Filippov et al. |
| 2008/0153138 A1 | 6/2008 | Livshits et al. |
| 2008/0261278 A1 | 10/2008 | Tabolina et al. |
| 2008/0261279 A1 | 10/2008 | Tabolina et al. |

FOREIGN PATENT DOCUMENTS

| EP | 0 301 572 | 2/1989 |
| WO | WO2007/139219 | 12/2007 |

OTHER PUBLICATIONS

Whitfield et al. Identification of res Genes in *Escherichia coli* O9:K30:H12 and Involvement in Regulation of Expression of Group IA K30 Capsular Polysaccharide, Methods in Molecular Genetics vol. 6, 1995, pp. 301-322.*
International Preliminary Report on Patentability for PCT Patent App. No. PCT/JP2007/061237 (Dec. 18, 2008).
U.S. Appl. No. 11/830,961, filed Jul. 31, 2007, Filippov et al.
U.S. Appl. No. 11/849,403, filed Sep. 4, 2007, Rybak et al.
U.S. Appl. No. 11/849,415, filed Sep. 4, 2007, Filippov et al.
U.S. Appl. No. 11/934,890, filed Nov. 5, 2007, Filippov et al.
U.S. Appl. No. 12/173,379, filed Jan. 22, 2008, Rybak et al.
U.S. Appl. No. 61/031,834, filed Feb. 27, 2008, Samsonov et al.
U.S. Appl. No. 61/053,704, filed May 16, 2008, Rybak et al.
U.S. Appl. No. 12/125,988, filed May 23, 2008, Filippov et al.
U.S. Appl. No. 12/212,743, filed Sep. 18, 2008, Rybak et al.
U.S. Appl. No. 12/253,415, filed Oct. 17, 2008, Filippov et al.
Ebel, W., et al., "*Escherichia coli* RcsA, a Positive Activator of Colanic Acid Capsular Polysaccharide Synthesis, Functions to Activate Its Own Expression," J. Bacteriol. 1999;181(2):577-584.

(Continued)

*Primary Examiner* — Iqbal H Chowdhury
(74) *Attorney, Agent, or Firm* — Shelly Guest Cermak; Cermak Nakajima LLP

(57) ABSTRACT

The present invention provides a method for producing an L-amino acid using a bacterium of the Enterobacteriaceae family, particularly a bacterium belonging to genus *Escherichia* or *Pantoea*, which has been modified to attenuate expression of the rcsA gene.

9 Claims, 2 Drawing Sheets

(56) References Cited

OTHER PUBLICATIONS

Jubete, Y., et al., "Role of the Heat Shock Protein DnaJ in the Lon-dependent Degradation of Naturally Unstable Proteins," J. Biol. Chem. 1996;271(48):30798-30803.

Stout, V., et al., "RscA, an Unstable Positive Regulator of Capsular Polysaccharide Synthesis," J. Bacteriol. 1991;173(5):1738-1747.

Wendisch, V. F., et al., "Metabolic engineering of *Escherichia coli* and *Corynebcterium glutamicum* for biotechnological production of organic acids and amino acids," Curr. Opinion Microbiol. 2006;9:268-274.

International Search Report and Written Opinion of the International Searching Authority for PCT Patent App. No. PCT/JP2007/061237 (Sep. 27, 2007).

\* cited by examiner

SEQUENCE LISTING

<160> NUMBER OF SEQ ID NOS: 6

<210> SEQ ID NO 1
<211> LENGTH: 624
<212> TYPE: DNA
<213> ORGANISM: Escherichia coli
<220> FEATURE:
<221> NAME/KEY: CDS
<222> LOCATION: (1)..(624)

<400> SEQUENCE: 1

```
atg tca acg att att atg gat tta tgt agt tac acc cga cta ggt tta      48
Met Ser Thr Ile Ile Met Asp Leu Cys Ser Tyr Thr Arg Leu Gly Leu
1               5                   10                  15 acc ggg tat ctg ttg agt aga ggg gtt aaa aaa aga gaa atc aac gac      96
Thr Gly Tyr Leu Leu Ser Arg Gly Val Lys Lys Arg Glu Ile Asn Asp
            20                  25                  30 att gaa acc gtt gat gac ctt gcc ata gct tgt gat tca cag cgc cct     144
Ile Glu Thr Val Asp Asp Leu Ala Ile Ala Cys Asp Ser Gln Arg Pro
        35                  40                  45 tca gtg gtg ttt att aat gag gac tgt ttc atc cac gat gct tct aac     192
Ser Val Val Phe Ile Asn Glu Asp Cys Phe Ile His Asp Ala Ser Asn
    50                  55                  60 agt cag cgt atc aag ctc atc att aat caa cat ccc aat acg tta ttt     240
Ser Gln Arg Ile Lys Leu Ile Ile Asn Gln His Pro Asn Thr Leu Phe
65                  70                  75                  80 atc gtt ttt atg gca att gcc aat gtt cat ttt gat gaa tat cta ttg     288
Ile Val Phe Met Ala Ile Ala Asn Val His Phe Asp Glu Tyr Leu Leu
                85                  90                  95 gtc aga aaa aat tta ttg atc agt tct aaa tcg att aaa ccg gaa tct     336
Val Arg Lys Asn Leu Leu Ile Ser Ser Lys Ser Ile Lys Pro Glu Ser
            100                 105                 110 ctc gac gat atc ctt ggc gat att ctg aaa aaa gag aca acg ata acc     384
Leu Asp Asp Ile Leu Gly Asp Ile Leu Lys Lys Glu Thr Thr Ile Thr
        115                 120                 125 tcg ttt tta aat atg ccg acg tta tca ttg agc cga acc gaa tcg agt     432
Ser Phe Leu Asn Met Pro Thr Leu Ser Leu Ser Arg Thr Glu Ser Ser
    130                 135                 140 atg ttg cga atg tgg atg gca ggt cag gga acc att caa atc tct gac     480
Met Leu Arg Met Trp Met Ala Gly Gln Gly Thr Ile Gln Ile Ser Asp
145                 150                 155                 160 caa atg aat atc aaa gcc aag acc gtt tca tcg cat aaa ggt aat att     528
Gln Met Asn Ile Lys Ala Lys Thr Val Ser Ser His Lys Gly Asn Ile
                165                 170                 175 aaa cgt aag atc aaa acg cat aat aaa cag gtt atc tac cat gtc gtc     576
Lys Arg Lys Ile Lys Thr His Asn Lys Gln Val Ile Tyr His Val Val
            180                 185                 190 cga ctg acg gat aat gtg act aat ggt att ttt gtc aac atg cgc taa     624
Arg Leu Thr Asp Asn Val Thr Asn Gly Ile Phe Val Asn Met Arg
        195                 200                 205
```

<210> SEQ ID NO 2
<211> LENGTH: 207
<212> TYPE: PRT
<213> ORGANISM: Escherichia coli

<400> SEQUENCE: 2

```
Met Ser Thr Ile Ile Met Asp Leu Cys Ser Tyr Thr Arg Leu Gly Leu
1               5                   10                  15
```

```
Thr Gly Tyr Leu Leu Ser Arg Gly Val Lys Lys Arg Glu Ile Asn Asp
        20                  25                  30

Ile Glu Thr Val Asp Asp Leu Ala Ile Ala Cys Asp Ser Gln Arg Pro
            35                  40                  45

Ser Val Val Phe Ile Asn Glu Asp Cys Phe Ile His Asp Ala Ser Asn
 50                  55                  60

Ser Gln Arg Ile Lys Leu Ile Ile Asn Gln His Pro Asn Thr Leu Phe
 65                  70                  75                  80

Ile Val Phe Met Ala Ile Ala Asn Val His Phe Asp Glu Tyr Leu Leu
                    85                  90                  95

Val Arg Lys Asn Leu Leu Ile Ser Ser Lys Ser Ile Lys Pro Glu Ser
                100                 105                 110

Leu Asp Asp Ile Leu Gly Asp Ile Leu Lys Lys Glu Thr Thr Ile Thr
            115                 120                 125

Ser Phe Leu Asn Met Pro Thr Leu Ser Leu Ser Arg Thr Glu Ser Ser
130                 135                 140

Met Leu Arg Met Trp Met Ala Gly Gln Gly Thr Ile Gln Ile Ser Asp
145                 150                 155                 160

Gln Met Asn Ile Lys Ala Lys Thr Val Ser Ser His Lys Gly Asn Ile
                165                 170                 175

Lys Arg Lys Ile Lys Thr His Asn Lys Gln Val Ile Tyr His Val Val
                180                 185                 190

Arg Leu Thr Asp Asn Val Thr Asn Gly Ile Phe Val Asn Met Arg
            195                 200                 205

<210> SEQ ID NO 3
<211> LENGTH: 57
<212> TYPE: DNA
<213> ORGANISM: Artificial
<220> FEATURE:
<223> OTHER INFORMATION: primer P1

<400> SEQUENCE: 3
atgtcaacga ttattatgga tttatgtagt tacacctagt aagccagtat acactcc       57

<210> SEQ ID NO 4
<211> LENGTH: 57
<212> TYPE: DNA
<213> ORGANISM: Artificial
<220> FEATURE:
<223> OTHER INFORMATION: primer P2

<400> SEQUENCE: 4
cagcctgact ggtgggaaac caccagtcag aatgtgttaa gggcaccaat aactgcc       57

<210> SEQ ID NO 5
<211> LENGTH: 21
<212> TYPE: DNA
<213> ORGANISM: Artificial
<220> FEATURE:
<223> OTHER INFORMATION: primer P3

<400> SEQUENCE: 5
tcgttacgca ttgagtgagg g                                              21

<210> SEQ ID NO 6
<211> LENGTH: 21
<212> TYPE: DNA
<213> ORGANISM: Artificial
<220> FEATURE:
<223> OTHER INFORMATION: primer P4
```

```
<400> SEQUENCE: 6
cggtatcttt gtggagaaag c                                          21
```

METHOD FOR PRODUCING AN L-AMINO ACID USING A BACTERIUM OF THE ENTEROBACTERIACEAE FAMILY WITH ATTENUATED EXPRESSION OF THE RCSA GENE

This application is a continuation under 35 U.S.C. §120 of PCT Patent Application No. PCT/JP2007/061237, filed May 28, 2007, which claims priority under 35 U.S.C. §119 to Russian Patent Application No. 2006118967, filed on Jun. 1, 2006, and U.S. Provisional Patent Application No. 60/868,102, filed Dec. 1, 2006, the entireties of which are incorporated by reference. The Sequence Listing filed electronically herewith is also hereby incorporated by reference in its entirety (File Name: US-289 Seq List; File Size: 6 KB; Date Created: Nov. 26, 2008).

FIELD OF THE INVENTION

The present invention relates to the microbiological industry, and specifically to a method for producing an L-amino acid using a bacterium of the Enterobacteriaceae family which has been modified to attenuate expression of the rcsA gene.

BRIEF DESCRIPTION OF THE RELATED ART

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170; 5,661,012 and 6,040,160).

Another way to enhance L-amino acid production yields is to attenuate expression of a gene or several genes involved in degradation of the target L-amino acid, genes diverting the precursors of the target L-amino acid from the L-amino acid biosynthetic pathway, genes involved in the redistribution of carbon, nitrogen, and phosphate fluxes, and genes coding for toxins etc.

The rcsA gene encodes the RcsA protein, which is an unstable positive regulator required for the synthesis of colanic acid capsular polysaccharide in *Escherichia coli*. Degradation of the RcsA protein in vivo depends on a ATP-dependent Lon protease. The DNA and protein sequences are highly homologous to a rcsA gene and a protein from *Klebsiella pneumoniae* and other species. The carboxy-terminal region of RcsA contains a potential helix-turn-helix DNA-binding motif which resembles the sequence found at the carboxy-terminus of RcsB, which is another positive regulator of capsule synthesis, and in several other transcriptional regulators including members of the LuxR family. The stability of wild-type RcsA in vivo is increased by the presence of multiple copies of RcsB, while RcsA is degraded more rapidly in rcsB mutant hosts than in wild-type hosts. These results suggest that RcsA and RcsB interact in vivo, and are consistent with genetic experiments that indicate an interaction between RcsA and RcsB (Stout, V. et. al., J. Bacteriol. 1991 March; 173(5): 1738-1747)).

RcsA is shown to activate its own expression, as seen by the 100-fold-increased expression of a rcsA::lacZ transcriptional fusion in strains with high levels of RcsA protein, either due to a mutation in lon or due to overexpression of RcsA from a multicopy plasmid. Expression of the rcsA::lacZ fusion is increased in the absence of RcsB. In addition, the effects of H—NS, a histone-like protein, and RcsB on the expression of rcsA are independent of each other. A sequence motif, conserved between the *E. coli* cps promoter and the *Erwinia amylovora* ams promoter and previously shown to be the RcsA-RcsB binding site, was identified in the rcsA promoter region and shown to be required for high-level expression of rcsA. (Ebel, W. and Trempy, J. E., J. Bacteriol., 181(2): 577-84 (1999)).

The role of DnaJ, a heat shock protein, in the degradation of RcsA was investigated. While the turnover of RcsA is slowed in dnaJ mutant hosts, the RcsA protein that accumulates is largely aggregated. The simultaneous stabilization and aggregation of RcsA are consistent with a model in which DnaJ (and possibly DnaK and GrpE as well) acts to stimulate proteolysis indirectly by helping to maintain RcsA in a soluble conformation. The effect of DnaJ on RcsA solubility is not limited to the protein overproduced from the plasmid. It was found that the chromosomally-encoded RcsA is mostly soluble in lon⁻ hosts but insoluble in lon⁻ dnaJ⁻ hosts; furthermore, insolubility is associated with a failure of RcsA to function in dnaJ mutants (Jubete, Y., et. al., J. Biol. Chem., 271(48), 30798-803 (1996)).

But currently, there have been no reports of attenuating expression of the rcsA gene for the purpose of producing L-amino acids.

SUMMARY OF THE INVENTION

Aspects of the present invention include enhancing the productivity of L-amino acid-producing strains and providing a method for producing an L-amino acid using these strains.

The above aspects were achieved by finding that attenuating expression of the rcsA gene can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the Enterobacteriaceae family which has an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an aspect of the present invention to provide an L-amino acid-producing bacterium of the Enterobacteriaceae family, wherein the bacterium has been modified to attenuate expression of the rcsA gene.

It is a further aspect of the present invention to provide the bacterium as described above, wherein the expression of the rcsA gene is attenuated by inactivation of the rcsA gene.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said L-amino acid is selected from the group consisting of an aromatic L-amino acid and a non-aromatic L-amino acid.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further aspect of the present invention to provide a method for producing an L-amino acid comprising:
cultivating the bacterium as described above in a medium, and
collecting said L-amino acid from the medium.

It is a further aspect of the present invention to provide the method as described above, wherein said L-amino acid is selected from the group consisting of an aromatic L-amino acid and a non-aromatic L-amino acid.

It is a further aspect of the present invention to provide the method as described above, wherein said aromatic L-amino acid is selected from the group consisting of L-phenylalanine, L-tyrosine, and L-tryptophan.

It is a further aspect of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

The present invention is described in detail below.

DETAILED DESCRIPTION OF THE PREFERRED EMBODIMENTS

1. Bacterium of the Present Invention

Figure 1:
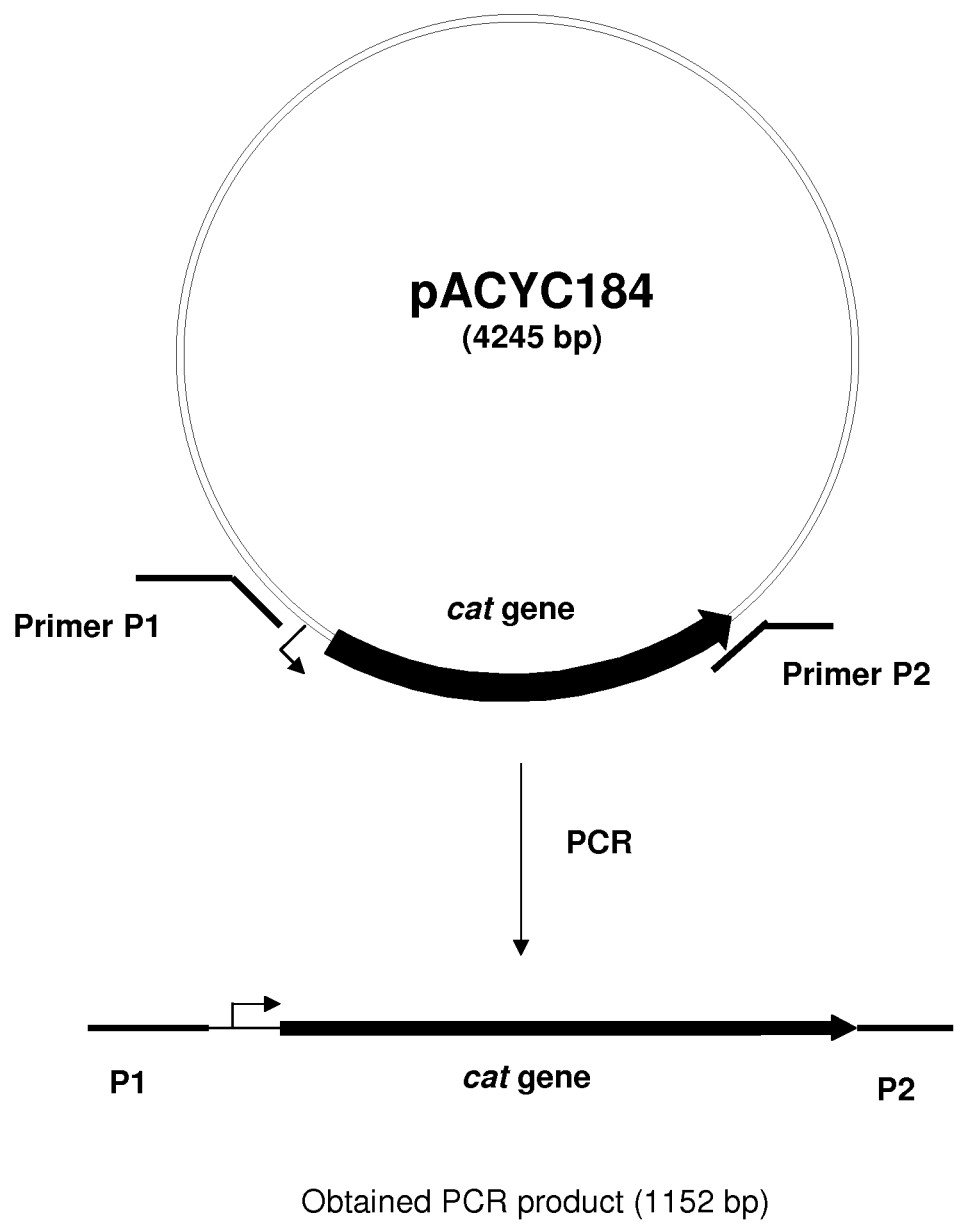
FIG. 1 shows the relative positions of primers P1 and P2 on plasmid pACYC184, which is used for amplification of the cat gene.

The bacterium of the present invention is an L-amino acid-producing bacterium of the Enterobacteriaceae family, wherein the bacterium has been modified to attenuate expression of the rcsA gene.

"L-amino acid-producing bacterium" means a bacterium which has an ability to produce and excrete an L-amino acid into a medium, when the bacterium is cultured in the medium.

The term "L-amino acid-producing bacterium" also means a bacterium which is able to produce and cause accumulation of an L-amino acid in a culture medium in an amount larger than a wild-type or parental strain of the bacterium, for example, E. coli, such as E. coli K-12, and preferably means that the bacterium is able to cause accumulation in a medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae according to the taxonomy used by the NCBI (National Center for Biotechnology Information) database (www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*). The bacterium belonging to the genus *Escherichia* is not particularly limited, however for example, bacteria described by Neidhardt, F. C. et al. (*Escherichia coli* and *Salmonella typhimurium*, American Society for Microbiology, Washington D.C., 1208, Table 1) are encompassed.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of the rcsA gene" means that the bacterium has been modified in such a way that the modified bacterium contains reduced amounts of the RcsA protein as compared with an unmodified bacterium, or the modified bacterium is unable to synthesize the RcsA protein.

The phrase "inactivation of the rcsA gene" means that the modified gene encodes a completely inactive protein. It is also possible that the modified DNA region is unable to naturally express the gene due to a deletion of a part of the gene or of the gene entirely, shifting of the reading frame of the gene, introduction of missense/nonsense mutation(s), or modification of an adjacent region of the gene, including sequences controlling gene expression, such as promoter(s), enhancer(s), attenuator(s), ribosome-binding site(s), etc.

The level of gene expression can be estimated by measuring the amount of mRNA transcribed from the gene using various known methods including Northern blotting, quantitative RT-PCR, and the like. The amount of the protein coded by the gene can be measured by known methods including SDS-PAGE followed by immunoblotting assay (Western blotting analysis) and the like.

The rcsA gene (synonyms-ECK1949, cpsR, b1951) encodes the RcsA protein (synonyms-CpsR, B1951). The rcsA gene of *E. coli* (nucleotides in positions 2,021,992 to 2,022,615 in the GenBank accession number NC_000913.2; gi:49175990; SEQ ID NO: 1) is located between the gene fliR and the gene dsrB on the chromosome of *E. coli* strain K-12. The nucleotide sequence of the rcsA gene and the amino acid sequence of RcsA encoded by the rcsA gene are shown in SEQ ID NO: 1 and SEQ ID NO: 2, respectively.

Since there may be some differences in DNA sequences between the genera or strains of the Enterobacteriaceae family, the rcsA gene to be inactivated on the chromosome is not limited to the gene shown in SEQ ID No:1, but may include genes homologous to SEQ ID No:1 which encode a variant protein of the RcsA protein. The phrase "variant protein" means a protein which has changes in the sequence, whether they are deletions, insertions, additions, or substitutions of amino acids, but still maintains the activity of the product as the RcsA protein. The number of changes in the variant protein depends on the position in the three dimensional structure of the protein or the type of amino acid residues. It may be 1 to 30, preferably 1 to 15, and more preferably 1 to 5 in SEQ ID NO: 2. These changes in the variants are conservative mutations that preserve the function of the protein. In other words, these changes in the variants can occur in regions of the protein which are not critical for the three dimensional structure of the protein. This is because some amino acids have high homology to one another so the three dimensional structure is not affected by such a change. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Specific examples of substitutions that are considered to be conservative include: substitution of Ala with Ser or Thr; substitution of Arg with Gln, His, or Lys; substitution of Asn with Glu, Gln, Lys, His, or Asp; substitution of Asp with Asn, Glu, or Gln; substitution of Cys with Ser or Ala; substitution of Gln with Asn, Glu, Lys, His, Asp, or Arg; substitution of Glu with Gly, Asn, Gln, Lys, or Asp; substitution of Gly with Pro; substitution of His with Asn, Lys, Gln, Arg, or Tyr; substitution of Ile with Leu, Met, Val, or Phe; substitution of Leu with Ile, Met, Val, or Phe; substitution of Lys with Asn, Glu, Gln, His, or Arg; substitution of Met with Ile, Leu, Val, or Phe; substitution of Phe with Trp, Tyr, Met, Ile, or Leu; substitution of Ser with Thr or Ala; substitution of Thr with Ser or Ala; substitution of Trp with Phe or Tyr; substitution of Tyr with His, Phe, or Trp; and substitution of Val with Met, Ile, or Leu. Substitutions, deletions, insertions, additions, or inversions and the like of the amino acids described above include naturally occurred mutations (mutant or variant) depending on differences in species, or individual differences of microorganisms that retain the rcsA gene. Such a gene can be obtained by modifying the nucleotide sequence shown in SEQ ID NO: 1 using, for example, site-directed mutagenesis, so that the site-specific amino acid residue in the protein encoded includes substitutions, deletions, insertions, or additions.

Moreover, the protein variant encoded by the rcsA gene may be one which has a homology of not less than 80%, preferably not less than 90%, and most preferably not less than 95%, with respect to the entire amino acid sequence shown in SEQ ID NO. 2.

Homology between two amino acid sequences can be determined using the well-known methods, for example, the computer program BLAST 2.0, which calculates three parameters: score, identity and similarity.

Moreover, the rcsA gene may be a variant which hybridizes under stringent conditions with the nucleotide sequence shown in SEQ ID NO: 1, or a probe which can be prepared from the nucleotide sequence under stringent conditions, provided that it encodes a functional RcsA protein prior to inactivation. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, in this specific case, it may be about 100 bp to 1 kbp.

Expression of the rcsA gene can be attenuated by introducing a mutation into the gene on the chromosome so that intracellular activity of the protein encoded by the gene is decreased as compared with an unmodified strain. Such a mutation on the gene can be replacement of one base or more to cause amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the rcsA gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity is prepared, and a bacterium to be modified is transformed with a DNA fragment containing the mutant gene. Then the native gene on the chromosome is replaced with the mutant gene by homologous recombination, and the resulting strain is selected. Such gene replacement using homologous recombination can be conducted by the method employing a linear DNA, which is known as "Red-driven integration" (Datsenko, K. A. and Wanner, B. L., Proc. Natl. Acad. Sci. USA, 97, 12, p 6640-6645 (2000), WO2005/010175), or by methods employing a plasmid containing a temperature-sensitive replication control region (Proc. Natl. Acad. Sci., USA, 97, 12, p 6640-6645 (2000), U.S. Pat. Nos. 6,303,383 and 5,616, 480). Furthermore, the introduction of a site-specific mutation by gene replacement using homologous recombination as set forth above can also be performed by using a plasmid lacking the ability to replicate in the host.

Expression of the gene can also be attenuated by insertion of a transposon or an IS factor into the coding region of the gene (U.S. Pat. No. 5,175,107), or by conventional methods, such as mutagenesis with UV irradiation or nitrosoguanidine (N-methyl-N'-nitro-N-nitrosoguanidine) treatment.

Inactivation of the gene can also be performed by conventional methods, such as by mutagenesis using UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45) also called "Red-driven integration".

The presence of the RcsA protein can be detected using polyclonal antibodies by the method described in (Ebel, W. and Trempy, J. E., J. Bacteriol., 181(2): 577-84 (1999)).

The presence or absence of the rcsA gene on the chromosome of a bacterium can be detected by well-known methods, including PCR, Southern blotting, and the like. In addition, the level of expression of a gene can be estimated by measuring the amount of mRNA transcribed from the gene using various well-known methods, including Northern blotting, quantitative RT-PCR, and the like. The amount or molecular weight of the protein encoded by the gene can be measured by well-known methods, including SDS-PAGE followed by immunoblotting assay (Western blotting analysis), and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

As a bacterium which is modified to attenuate expression of the rcsA gene, bacteria which are able to produce either an aromatic or a non-aromatic L-amino acids may be used.

The bacterium can be obtained by attenuating expression of the rcsA gene in a bacterium which inherently has the ability to produce L-amino acids. Alternatively, the bacterium can be obtained by imparting the ability to produce L-amino acids to a bacterium already having the attenuated expression of the rcsA gene.

L-Threonine-Producing Bacteria

Examples of parent strains for deriving the L-threonine-producing bacteria include, but are not limited to, strains belonging to the genus *Escherichia*, such as *E. coli* TDH-6/pVIC40 (VKPM B-3996) (U.S. Pat. Nos. 5,175,107, 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow, 1 Dorozhny proezd, 1) on Apr. 7, 1987 under the accession number VKPM B-3996.

*E. coli* VKPM B-5318 (EP 0593792B) may also be used as a parent strain for deriving L-threonine-producing bacteria. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium is additionally modified to enhance expression of one or more of the following genes:
the mutant thrA gene which codes for aspartokinase homoserine dehydrogenase I resistant to feed back inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region which affects the transcription is removed from the operon (WO2005/049808, WO2003/097839).

A mutant thrA gene which codes for aspartokinase homoserine dehydrogenase I resistant to feed back inhibition by threonine, as well as the thrB and thrC genes can be obtained as one operon from the well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position-1 with respect to the ATG start codon (ABSTRACTS of the 17th International Congress of Biochemistry and Molecular Biology in conjugation with the Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue include, but are not limited to, oxalysine, lysine hydroxamate, S-(2-aminoethyl)-L-cysteine (AEC), γ-methyllysine, α-chlorocaprolactam, and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenease (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827,698), and the malic enzyme L-Cysteine-Producing Bacteria Examples of parent strains for deriving L-cysteine-producing bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains for deriving L-leucine-producing bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium may be improved by enhancing the expression of one or more genes involved in L-leucine biosynthesis. Examples include genes of the leuABCD operon, which are preferably represented by a mutant leuA gene coding for isopropylmalate synthase which is freed from feedback inhibition by L-leucine (U.S. Pat. No. 6,403,342). In addition, the bacterium may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* A180/pFM201 (U.S. Pat. No. 6,258,554) and the like.

Examples of parent strains for deriving L-histidine-producing bacteria also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation into ATP phosphoribosyltransferase which imparts resistance to the feedback inhibition (Russian Patent Nos. 2003677 and 2119536).

Specific examples of strains having an L-histidine-producing ability include *E. coli* FERM P-5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria include, but are not limited to, strains belonging to the genus *Escherichia*, such as *E. coli* VL334thrC⁺ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 which was grown on wild-type *E. coli* K12 (VKPM B-7) cells. As a result, an L-isoleucine auxotrophic strain VL334thrC⁺ (VKPM B-8961), which is able to produce L-glutamic acid, was obtained.

Examples of parent strains for deriving the L-glutamic acid-producing bacteria include, but are not limited to, strains which are deficient in α-ketoglutarate dehydrogenase activity, or strains in which one or more genes encoding an L-glutamic acid biosynthetic enzyme are enhanced. Examples of the genes involved in L-glutamic acid biosynthesis include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate carboxylase (pyc), pyruvate dehydrogenase (aceEF, lpdA), pyruvate kinase (pyka, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of strains which have been modified so that expression of the citrate synthetase gene and/or the phosphoenolpyruvate carboxylase gene are reduced, and/or/are deficient in α-ketoglutarate dehydrogenase activity include those disclosed in EP1078989A, EP955368A, and EP952221A.

Examples of parent strains for deriving the L-glutamic acid-producing bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W311 OsucA:: Km^R
*E. coli* AJ12624 (FERM BP-3853)
*E. coli* AJ12628 (FERM BP-3854)
*E. coli* AJ12949 (FERM BP-4881)

*E. coli* W3110sucA::Km^R is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in α-ketoglutarate dehydrogenase activity or have decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria include, but are not limited to, strains belonging to the genus *Escherichia*, such as *E. coli* JP4735/pMU3028 (DSM10122) and JP6015/pMU91 (DSM10123) which is deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180, 373); *E. coli* AGX17 (pGX44) (NRRL B-12263) and AGX6 (pGX50) aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the identified protein encoded by and the yedA gene or the yddG gene may also be used (U.S. patent applications 2003/0148473 A1 and 2003/0157667 A1).

Examples of parent strains for deriving the L-tryptophan-producing bacteria also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase. The tryptophan synthase consists of $\alpha$ and $\beta$ subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433). The bacterium may be improved by enhancing the expression of one or more genes involved in L-proline biosynthesis. Examples of such genes for L-proline producing bacteria include the proB gene coding for glutamate kinase which has feedback inhibition by L-proline desensitized (DE Patent 3127361). In addition, the bacterium may be improved by enhancing the expression of one or more genes coding for proteins excreting L-amino acid from bacterial cell. Such genes are exemplified by the b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains for deriving L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased.

Examples of parent strains for deriving L-valine-producing bacteria include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 117545 Moscow, 1 Dorozhny Proezd, 1) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains for deriving L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

The method of the present invention is a method for producing an L-amino acid by cultivating the bacterium in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

The chosen culture medium may be either a synthetic or natural medium, so long as it includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganisms can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as by shaking and/or stirring with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated rcsA Gene

1. Deletion of the rcsA Gene.

The rcsA gene was deleted by the method initially developed by Datsenko, K. A. and Wanner, B. L. (Proc. Natl. Acad. Sci. USA, 2000, 97(12), 6640-6645) called "Red-driven integration". According to this procedure, the PCR primers P1 (SEQ ID NO: 3) and P2 (SEQ ID NO: 4), which are complementary to both the region adjacent to the rcsA gene and the gene conferring antibiotic resistance, respectively, in the template plasmid, were constructed. The plasmid pACYC184 (NBL Gene Sciences Ltd., UK) (GenBank/EMBL accession number X06403) was used as a template in the PCR reaction. Conditions for PCR were as follows: denaturation step:3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

An 1152 bp PCR product (FIG. 1) was obtained and purified in agarose gel and used for electroporation of E. coli MG1655 (ATCC 700926), which contains the plasmid pKD46 having a temperature-sensitive replication. The plasmid pKD46 (Datsenko, K. A. and Wanner, B. L., Proc. Natl. Acad. Sci. USA, 2000, 97:12:6640-45) includes a 2,154 nucleotide (31088-33241) DNA fragment of phage λ (GenBank accession No. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from American Type Culture Collection. (P.O. Box 1549 Manassas, Va. 20108, U.S.A.).

Electrocompetent cells were prepared as follows: E. coli MG1655/pKD46 was grown overnight at 30° C. in LB medium containing ampicillin (100 mg/l), and the culture was diluted 100 times with 5 ml of SOB medium (Sambrook et al, "Molecular Cloning A Laboratory Manual, Second Edition", Cold Spring Harbor Laboratory Press (1989)) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 µl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 hours and were then plated onto L-agar containing chloramphenicol (30 µg/ml) and grown at 37° C. to select $Cm^R$ recombinants. Then, to eliminate the pKD46 plasmid, 2 passages on L-agar with Cm at 42° C. were performed and the obtained colonies were tested for sensitivity to ampicillin.

2. Verification of the rcsA Gene Deletion by PCR.

Figure 2:
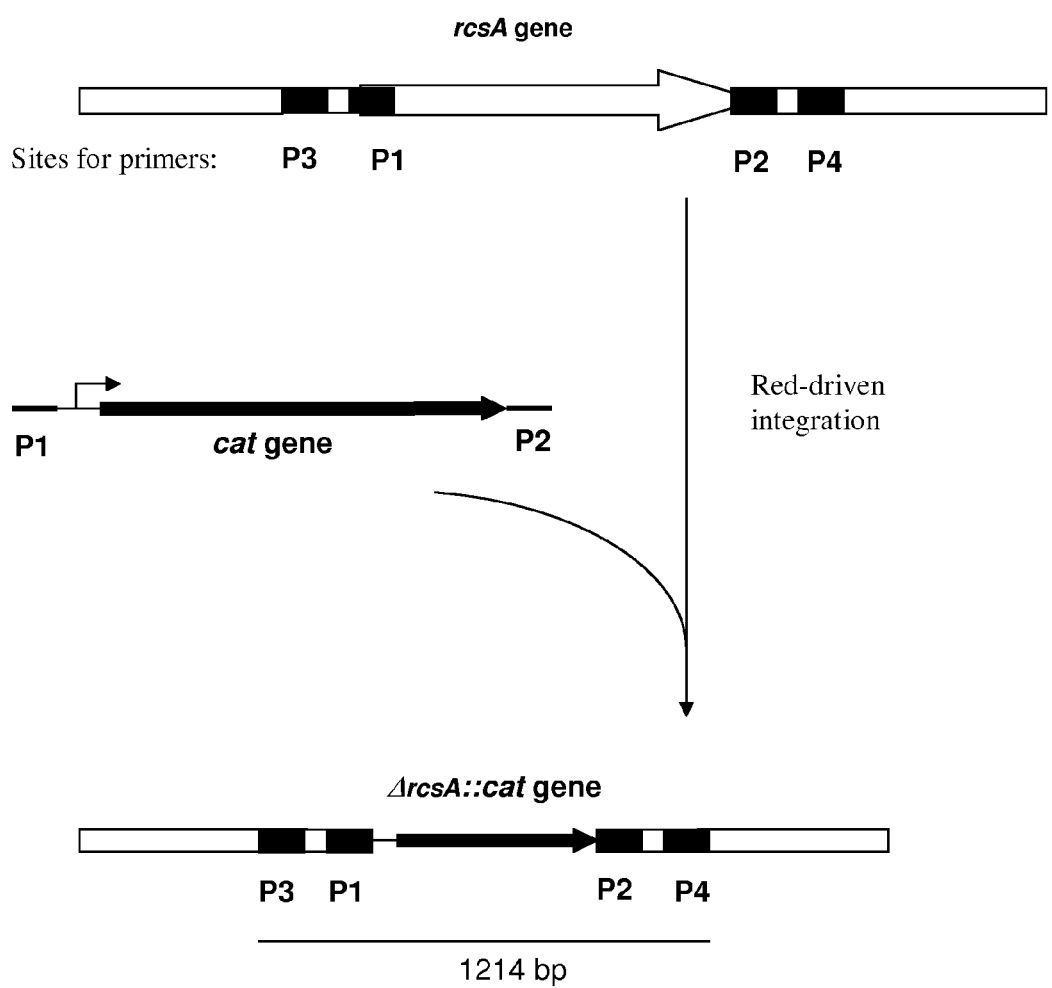
FIG. 2 shows the construction of the chromosomal DNA fragment comprising the inactivated rcsA-gene.

The mutants, which have the rcsA gene deleted and are marked with the Cm resistance gene, were verified by PCR. Locus-specific primers P3 (SEQ ID NO: 5) and P4 (SEQ ID NO: 6) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained using the parental rcsA⁺ strain MG1655 as the template, is 722 bp in length. The PCR product obtained using the mutant strain as the template is 1214 nucleotides in length (FIG. 2). The mutant strain was named MG1655 Δ rcsA::cat.

Example 2

Production of L-threonine by E. coli strain B-3996-ΔrcsA

To test the effect of inactivation of the rcsA gene on threonine production, DNA fragments from the chromosome of the above-described E. coli MG1655 ΔrcsA::cat were transferred to the threonine-producing E. coli strain VKPM B-3996 by P1 transduction (Miller, J. H. Experiments in Molecular Genetics, Cold Spring Harbor Lab. Press, 1972, Plainview, N.Y.) to obtain the strain B-3996-ΔrcsA. The strain B-3996 was deposited on Nov. 19, 1987 in the All-Union Scientific Center of Antibiotics (Russia, 117105 Moscow, Nagatinskaya Street, 3-A) under the accession number RIA 1867. The strain was also deposited in the Russian National Collection of Industrial Microorganisms (VKPM) (Russia, 117545 Moscow, 1 Dorozhny proezd, 1) under the accession number VKPM B-3996.

Both E. coli B-3996 and B-3996-ΔrcsA, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) of seed material. The fermentation was performed in 2 ml of minimal medium for fermentation in 20×200-mm test tubes. Cells were grown for 65 hours at 32° C. with shaking at 250 rpm.

After cultivation, the amount of L-threonine, which had accumulated in the medium, was determined by paper chromatography using the following mobile phase: butanol:acetic acid:water=4:1:1 (v/v). A solution 2% of ninhydrin in acetone was used as a visualizing reagent. A spot containing L-threonine was cut out, L-threonine was eluted in 0.5% water solution of $CdCl_2$, and the amount of L-threonine was estimated spectrophotometrically at 540 nm. The results of 8 independent test tube fermentations are shown in Table 1. As follows from Table 1, B-3996-ΔrcsA caused accumulation of a higher amount of L-threonine, as compared with B-3996.

The composition of the fermentation medium (g/l) was as follows:

| | |
|---|---|
| Glucose | 80.0 |
| (NH$_4$)$_2$SO$_4$ | 22.0 |
| NaCl | 0.8 |
| KH$_2$PO$_4$ | 2.0 |
| MgSO$_4$·7H$_2$O | 0.8 |
| FeSO$_4$·7H$_2$O | 0.02 |
| MnSO$_4$·5H$_2$O | 0.02 |
| Thiamine HCl | 0.0002 |
| Yeast extract | 1.0 |
| CaCO$_3$ | 30.0 |

Glucose and magnesium sulfate were sterilized separately. CaCO$_3$ was sterilized by dry-heat at 180° C. for 2 hours. The pH was adjusted to 7.0. The antibiotic was introduced into the medium after sterilization.

TABLE 1

| Strain | OD$_{540}$ | Amount of L-threonine, g/l |
|---|---|---|
| B-3996 | 29.4 ± 0.7 | 25.9 ± 0.7 |
| B-3996-ΔrcsA | 29.8 ± 0.5 | 27.7 ± 0.8 |

Example 3

Production of L-lysine by *E. coli* AJ11442-ΔrcsA

To test the effect of inactivation of the rcsA gene on lysine production, DNA fragments from the chromosome of the above-described *E. coli* strain MG1655 ΔrcsA::cat can be transferred to the lysine-producing *E. coli* strain AJ11442 by P1 transduction (Miller, J. H. Experiments in Molecular Genetics, Cold Spring Harbor Lab. Press, 1972, Plainview, N.Y.) to obtain AJ11442-ΔrcsA strain. The strain AJ14442 was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on May 1, 1981 and received an accession number of FERM P-5084. Then, it was converted to an international deposit under the provisions of the Budapest Treaty on Oct. 29, 1987, and received an accession number of FERM BP-1543.

Both *E. coli* strains, AJ11442 and AJ11442-ΔrcsA, can be cultured in L-medium containing streptomycin (20 mg/l) at 37° C., and 0.3 ml of the obtained culture can be inoculated into 20 ml of the fermentation medium containing the required drugs in a 500-ml flask. The cultivation can be carried out at 37° C. for 16 h by using a reciprocal shaker at the agitation speed of 115 rpm. After the cultivation, the amounts of L-lysine and residual glucose in the medium can be measured by a known method (Biotech-analyzer AS210 manufactured by Sakura Seiki Co.). Then, the yield of L-lysine can be calculated relative to consumed glucose for each of the strains.

The composition of the fermentation medium (g/l) is as follows:

| | |
|---|---|
| Glucose | 40 |
| (NH$_4$)$_2$SO$_4$ | 24 |
| K$_2$HPO$_4$ | 1.0 |
| MgSO$_4$·7H$_2$O | 1.0 |
| FeSO$_4$·7H$_2$O | 0.01 |

-continued

| | |
|---|---|
| MnSO$_4$·5H$_2$O | 0.01 |
| Yeast extract | 2.0 |

The pH is adjusted to 7.0 by KOH and the medium is autoclaved at 115° C. for 10 min. Glucose and MgSO$_4$·7H$_2$O are sterilized separately. CaCO$_3$ is dry-heat sterilized at 180° C. for 2 hours and added to the medium for a final concentration of 30 μl.

Example 4

Production of L-cysteine by *E. coli* JM15 (ydeD)-ΔrcsA

To test the effect of inactivation of the rcsA gene on L-cysteine production, DNA fragments from the chromosome of the above-described *E. coli* MG1655 ΔrcsA::cat can be transferred to the *E. coli* L-cysteine-producing strain JM15 (ydeD) by P1 transduction (Miller, J. H. Experiments in Molecular Genetics, Cold Spring Harbor Lab. Press, 1972, Plainview, N.Y.) to obtain the strain JM15 (ydeD)-ΔrcsA.

*E. coli* JM15 (ydeD) is a derivative of *E. coli* JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663). The strain JM15 (CGSC# 5042) can be obtained from The Coli Genetic Stock Collection at the *E. coli* Genetic Resource Center, MCD Biology Department, Yale University (cgsc.biology.yale.edu/).

Fermentation conditions for evaluation of L-cysteine production were described in detail in Example 6 of U.S. Pat. No. 6,218,168.

Example 5

Production of L-leucine by *E. coli* 57-ΔrcsA

To test the effect of inactivation of the rcsA gene on L-leucine production, DNA fragments from the chromosome of the above-described *E. coli* strain MG1655 ΔrcsA::cat can be transferred to the *E. coli* L-leucine-producing strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-pMW-ΔrcsA. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* strains, 57 and 57-ΔrcsA, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic acid-water=4:1:1).

The composition of the fermentation medium (g/l) (pH 7.2) is as follows:

| | |
|---|---|
| Glucose | 60.0 |
| (NH$_4$)$_2$SO$_4$ | 25.0 |
| K$_2$HPO$_4$ | 2.0 |
| MgSO$_4$·7H$_2$O | 1.0 |
| Thiamine | 0.01 |
| CaCO$_3$ | 25.0 |

Glucose and CaCO$_3$ are sterilized separately.

Example 6

Production of L-histidine by E. coli 80-ΔrcsA

To test the effect of inactivation of the rcsA gene on L-histidine production, DNA fragments from the chromosome of the above-described E. coli MG1655 ΔrcsA::cat can be transferred to the histidine-producing E. coli strain 80 by P1 transduction (Miller, J. H. Experiments in Molecular Genetics, Cold Spring Harbor Lab. Press, 1972, Plainview, N.Y.) to obtain strain 80-ΔrcsA. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

Both E. coli strains, 80 and 80-ΔrcsA, can each be cultured in L-broth for 6 h at 29° C. Then, 0.1 ml of obtained culture can be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol: acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 of as total nitrogen |
| L-proline | 1.0 |
| (NH$_4$)$_2$SO$_4$ | 25.0 |
| KH$_2$PO$_4$ | 2.0 |
| MgSO$_4$·7H$_2$O | 1.0 |
| FeSO$_4$·7H$_2$O | 0.01 |
| MnSO$_4$ | 0.01 |
| Thiamine | 0.001 |
| Betaine | 2.0 |
| CaCO$_3$ | 60.0 |

Glucose, proline, betaine and CaCO$_3$ are sterilized separately. The pH is adjusted to 6.0 before sterilization.

Example 7

Production of L-glutamate by E. coli VL334thrC$^+$-ΔrcsA

To test the effect of inactivation of the rcsA gene on L-glutamate production, DNA fragments from the chromosome of the above-described E. coli strain MG1655 ΔrcsA::cat can be transferred to the E. coli L-glutamate-producing strain VL334thrC$^+$ (EP 1172433) by P1 transduction (Miller, J. H. Experiments in Molecular Genetics, Cold Spring Harbor Lab. Press, 1972, Plainview, N.Y.) to obtain the strain VL334thrC$^+$-ΔrcsA. The strain VL334thrC$^+$ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both strains, VL334thrC$^+$ and VL334thrC$^+$-ΔrcsA, can be grown for 18-24 hours at 37° C. on L-agar plates. Then, one loop of the cells can be transferred into test tubes containing 2 ml of fermentation medium. The fermentation medium contains glucose (60 g/l), ammonium sulfate (25 g/l), KH$_2$PO$_4$ (2 g/l), MgSO$_4$ (1 g/l), thiamine (0.1 mg/ml), L-isoleucine (70 μg/ml), and CaCO$_3$ (25 g/l). The pH is adjusted to 7.2. Glucose and CaCO$_3$ are sterilized separately. Cultivation can be carried out at 30° C. for 3 days with shaking. After the cultivation, the amount of L-glutamic acid which is produced can be determined by paper chromatography (liquid phase composition of butanol-acetic acid-water=4:1:1) with subsequent staining by ninhydrin (1% solution in acetone) and further elution of the compounds in 50% ethanol with 0.5% CdCl$_2$.

Example 8

Production of L-phenylalanine by E. coli AJ12739-ΔrcsA

To test the effect of inactivation of the rcsA gene on L-phenylalanine production, DNA fragments from the chromosome of the above-described E. coli MG1655 ΔrcsA::cat can be transferred to the phenylalanine-producing E. coli strain AJ12739 by P1 transduction (Miller, J. H. Experiments in Molecular Genetics, Cold Spring Harbor Lab. Press, 1972, Plainview, N.Y.) to obtain strain AJ12739-ΔrcsA. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197 and then converted to a deposit under the Budapest Treaty on Aug. 23, 2002.

Both strains, AJ12739-ΔrcsA and AJ12739, can be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| (NH$_4$)$_2$SO$_4$ | 16.0 |
| K$_2$HPO$_4$ | 0.1 |
| MgSO$_4$·7H$_2$O | 1.0 |
| FeSO$_4$·7H$_2$O | 0.01 |
| MnSO$_4$ 5H$_2$O | 0.01 |
| Thiamine HCl | 0.0002 |
| Yeast extract | 2.0 |
| Tyrosine | 0.125 |
| CaCO$_3$ | 20.0 |

Glucose and magnesium sulfate are sterilized separately. $CaCO_3$ is dry-heat sterilized at 180° for 2 hours. The pH is adjusted to 7.0.

Example 9

Production of L-tryptophan by E. coli SV164 (pGH5)-ΔrcsA

To test the effect of inactivation of the rcsA gene on L-tryptophan production, DNA fragments from the chromosome of the above-described E. coli strain MG1655 ΔrcsA::cat can be transferred to the tryptophan-producing E. coli strain SV164 (pGH5) by P1 transduction (Miller, J. H. Experiments in Molecular Genetics, Cold Spring Harbor Lab. Press, 1972, Plainview, N.Y.) to obtain the strain SV164 (pGH5)-ΔrcsA. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) was described in detail in U.S. Pat. No. 6,180,373 or European patent 0662143.

Both strains, SV164 (pGH5)-ΔrcsA and SV164 (pGH5), can each be cultivated with shaking at 37° C. for 18 hours in 3 ml of nutrient broth supplemented with tetracycline (20 mg/l, marker of pGH5 plasmid). The obtained cultures (0.3 ml each) can be inoculated into 3 ml of a fermentation medium containing tetracycline (20 mg/l) in 20×200-mm test tubes, and cultivated at 37° C. for 48 hours with a rotary shaker at 250 rpm. After cultivation, the amount of tryptophan which accumulates in the medium can be determined by TLC as described in Example 8. The fermentation medium components are listed in Table 2, but should be sterilized in separate groups (A, B, C, D, E, F, and H), as shown, to avoid adverse interactions during sterilization.

TABLE 2

| Groups | Component | Final concentration, g/l |
|---|---|---|
| A | $KH_2PO_4$ | 1.5 |
|  | NaCl | 0.5 |
|  | $(NH_4)_2SO_4$ | 1.5 |
|  | L-Methionine | 0.05 |
|  | L-Phenylalanine | 0.1 |
|  | L-Tyrosine | 0.1 |
|  | Mameno (total N) | 0.07 |
| B | Glucose | 40.0 |
|  | $MgSO_4 \cdot 7H_2O$ | 0.3 |
| C | $CaCl_2$ | 0.011 |
| D | $FeSO_4 \cdot 7H_2O$ | 0.075 |
|  | Sodium citrate | 1.0 |
| E | $Na_2MoO_4 \cdot 2H_2O$ | 0.00015 |
|  | $H_3BO_3$ | 0.0025 |
|  | $CoCl_2 \cdot 6H_2O$ | 0.00007 |
|  | $CuSO_4 \cdot 5H_2O$ | 0.00025 |
|  | $MnCl_2 \cdot 4H_2O$ | 0.0016 |
|  | $ZnSO_4 \cdot H_2O$ | 0.0003 |
| F | Thiamine HCl | 0.005 |
| G | $CaCO_3$ | 30.0 |
| H | Pyridoxine | 0.03 |

Group A had pH 7.1 adjusted by $NH_4OH$. Each group is sterilized separately, chilled, and then mixed together.

Example 10

Production of L-proline by E. coli 702ilvA-ΔrcsA

To test the effect of inactivation of the rcsA gene on L-proline production, DNA fragments from the chromosome of the above-described E. coli strain MG1655 ΔrcsA::cat can be transferred to the proline-producing E. coli strain 702ilvA by P1 transduction (Miller, J. H. Experiments in Molecular Genetics, Cold Spring Harbor Lab. Press, 1972, Plainview, N.Y.) to obtain the strain 702ilvA-ΔrcsA. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli strains, 702ilvA and 702ilvA-ΔrcsA, can be grown for 18-24 hours at 37° C. on L-agar plates. Then, these strains can be cultivated under the same conditions as in Example 8.

Example 11

Production of L-arginine by E. coli 382-ΔrcsA

To test the effect of inactivation of the rcsA gene on L-arginine production, DNA fragments from the chromosome of the above-described E. coli strain MG1655 ΔrcsA::cat can be transferred to the arginine-producing E. coli strain 382 by P1 transduction (Miller, J. H. Experiments in Molecular Genetics, Cold Spring Harbor Lab. Press, 1972, Plainview, N.Y.) to obtain strain 382-ΔrcsA. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both strains, 382-ΔrcsA and 382, can be separately cultivated with shaking at 37° C. for 18 hours in 3 ml of nutrient broth, and 0.3 ml of the obtained cultures can be inoculated into 2 ml of a fermentation medium in 20×200-mm test tubes and cultivated at 32° C. for 48 hours on a rotary shaker.

After the cultivation, the amount of L-arginine which accumulated in the medium can be determined by paper chromatography using the following mobile phase: butanol:acetic acid:water=4:1:1 (v/v). A solution of ninhydrin (2%) in acetone can be used as a visualizing reagent. A spot containing L-arginine can be cut out, L-arginine can be eluted with 0.5% water solution of $CdCl_2$, and the amount of L-arginine can be estimated spectrophotometrically at 540 nm.

The composition of the fermentation medium (g/l) is as follows:

| | |
|---|---|
| Glucose | 48.0 |
| $(NH4)_2SO_4$ | 35.0 |
| $KH_2PO_4$ | 2.0 |
| $MgSO_4 \cdot 7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180° C. for 2 hours. The pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

Industrial Applicability

According to the present invention, production of an L-amino acid by a bacterium of the Enterobacteriaceae family can be enhanced.

The invention claimed is:

1. A method for producing an L-amino acid comprising:
   A) cultivating an L-amino acid-producing *Escherichia coli* bacterium in a medium, and
   B) collecting said L-amino acid from the medium in an amount of not less than 0.5 g/L,
   wherein said bacterium has been modified to attenuate expression of the *Escherichia coli* rcsA gene located on the chromosome of said bacterium by a method selected from the group consisting of:
   a) deleting a part of the rcsA gene,
   b) shifting the reading frame of the rcsA gene,
   c) introducing one or more missense/nonsense mutations into the rcsA gene,
   d) modifying sequences controlling gene expression of the rcsA gene, and
   e) combinations thereof.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

5. The method according to claim 1, wherein said rcsA gene encodes a protein having a homology of not less than 95% to the amino acid sequence of SEQ ID NO: 2.

6. The method according to claim 5, wherein said L-amino acid is selected from the group consisting of an aromatic L-amino acid and a non-aromatic L-amino acid.

7. The method according to claim 6, wherein said aromatic L-amino acid is selected from the group consisting of L-phenylalanine, L-tyrosine, and L-tryptophan.

8. The method according to claim 6, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

9. A method for producing an L-amino acid comprising:
   A) cultivating an L-amino acid-producing *Escherichia coli* bacterium in a medium, and
   B) collecting said L-amino acid from the medium in an amount of not less than 0.5 g/L,
   wherein said bacterium has been modified to attenuate expression of the *Escherichia coli* rcsA gene located on the chromosome of said bacterium by a method selected from the group consisting of:
   a) deleting a part of or the entire rcsA gene,
   b) shifting the reading frame of the rcsA gene,
   c) introducing one or more missense/nonsense mutations into the rcsA gene,
   d) modifying sequences controlling gene expression of the rcsA gene, and
   e) combinations thereof.

\* \* \* \* \*